US00PP31682P2

(12) United States Plant Patent
Meilland

(10) Patent No.: US PP31,682 P2
(45) Date of Patent: Apr. 21, 2020

(54) GRANDIFLORA ROSE PLANT NAMED 'MEISISTOMA'

(50) Latin Name: *Rosa hybrida*
Varietal Denomination: MEISISTOMA

(71) Applicant: THE CONARD-PYLE COMPANY, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,630

(22) Filed: Dec. 12, 2018

(51) Int. Cl.
*A01H 5/02* (2018.01)
*A01H 6/74* (2018.01)

(52) U.S. Cl.
USPC ..... Plt./132

(58) Field of Classification Search
USPC ..... Plt./101, 141, 143, 130, 131
See application file for complete search history.

(56) References Cited

U.S. PATENT DOCUMENTS

| | | | |
|---|---|---|---|
| PP14,731 | P3 | 4/2004 | Twomey et al. |
| PP18,102 | P2 | 10/2007 | Lim |
| PP27,894 | P3 | 4/2017 | Meilland |

*Primary Examiner* — Susan McCormick Ewoldt
*Assistant Examiner* — Karen M Redden
(74) *Attorney, Agent, or Firm* — Buchanan Ingersoll & Rooney PC

(57) ABSTRACT

A new and distinct variety of bedding rose plant, herein referred to by its cultivar name, 'MEISISTOMA', is provided which forms very abundantly on a nearly continuous basis attractive, cup shaped yellow amply suffused with red colored flowers that intensifies in red coloration gradually during the course of opening. Attractive, semi-glossy, very dense foliage is formed, which contrasts beautifully with the blossoms. A semi-erected growth habit is displayed. The disease tolerance is good, particularly against black spot. The new variety is well suited for proving attractive ornamentation in the landscape.

1 Drawing Sheet

Botanical/commercial classification:
Latin name—*Rosa hybrida.*
Common name—Grandiflora Rose Plant.
Varietal denomination—'MEISISTOMA'.

SUMMARY OF THE INVENTION

The new variety of *Rosa hybrida* Grandiflora Rose plant was created by artificial pollination wherein two parents were crossed which previously had been studied in the hope that they would contribute the desired characteristics. The female parent (i.e., the seed parent) was the 'BAICENT' variety (U.S. Plant Pat. No. 18,102). The male parent (i.e., the pollen parent) was the 'BAIPEACE' variety (U.S. Plant Pat. No. 14,731).

The parentage of the new variety can be summarized as follows:

'BAICENT' x 'BAIPEACE'

The seeds resulting from the above pollination were sown and small plants were obtained which were physically and biologically different from each other. Selective study resulted in the identification of a single plant of the new variety.

It was found that the new variety of Grandiflora Rose plant of the present invention possesses the following combination of characteristics:

(a) forms attractive, cup shaped, yellow amply suffused with red colored flowers, wherein the red coloration intensifies gradually in the course of opening,
(b) provides, very dense, semi-glossy foliage, (c) exhibits good tolerance to diseases, particularly against black spot, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'BAICENT' variety (i.e., the seed parent) displays yellow colored flowers and the 'BIAPEACE' variety (i.e., the pollen parent) displays yellow blend colored flowers highlighted with pink, whereas the new variety displays yellow amply suffused with red colored flowers, which intensifies red coloration gradually in the course of the flower opening. Moreover, new variety can be readily distinguished from related similar non-parental varieties. For example, the 'Meianycid' variety (U.S. Plant Pat. No. 27,894) displays flowers that remain yellow throughout the course of the flower opening, whereas the new variety displays yellow amply suffused with red colored flowers, which intensifies red coloration gradually in the course of the flower opening.

The new variety has been found to undergo asexual propagation in Le Cannet des Maures, Var, France by a number of routes, including budding, grafting, and the use of cuttings. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEISISTOMA'.

BRIEF DESCRIPTION OF THE PHOTOGRAPH

The accompanying photograph of FIG. 1 shows as nearly true as it is reasonably possible to make the same, in a color illustration of this character, typical specimens of the plant parts of the new variety. The rose plants of the new variety were approximately two years of age and were observed during June while budded on their own roots and growing outdoors at Le Cannet des Maures, Var, France. Dimensions in centimeters are indicated at the bottom of FIG. 1.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the pistils (stamens removed).

Element 11—illustrates a specimen of a floral receptacle showing arrangement of the stamens and pistils.

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—upper surface.

Element 15—illustrates a specimen of a leaf with 7 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of two-year-old specimens of the new variety during June while budded on their own roots and growing outdoors at Le Cannet des Maures, Var, France. Commercial classification: Grandiflora Rose Plant.

Plant:

*Habit*.—Semi-erected.

*Height*.—Commonly between 80 to 90 cm on average.

*Width*.—Commonly between 60 to 70 cm on average.

Branches:

*Color*.—Young stems: commonly near Green Group 138A. Adult wood: commonly near Yellow-Green Group 146B.

*Thorns*.—Configuration on adult stems: curved downwards on the upper surface and concave on the under surface. Long prickles (≥0.5 cm) — quantity: commonly approximately 3 thorns per 10 cm long young stem and commonly 5 thorns per 10 cm long adult stem. Long prickles (≥0.5 cm) — base shape: oval. Long prickles (≥0.5 cm) — size: commonly near 0.5 cm in length on average on young stems and commonly near 1.4 cm on average on adult stems. Long prickles (≥0.5 cm) — color: commonly near Yellow-Green Group 151D on young stems and commonly near Greyed-Orange Group 164A on adult stems. Small prickles (<0.5 cm) — quantity: commonly approximately 5 thorns per 10 cm long young stem and none observed on adult stem. Small prickles (<0.5 cm) — base shape: oval. Small prickles (<0.5 cm) — size: commonly near 0.2 cm in length on average on young stems. Small prickles (<0.5 cm) — color: commonly near Yellow-Green Group 151D on young stems.

Foliage:

*General appearance*.—Very dense with a semi-glossy aspect.

*Number of leaflets*.—3, 5, and 7; most often 5 and 7.

*Terminal leaflet*.—Length: approximately 5.5 cm on average. Width: approximately 4.5 cm on average.

*New foliage*.—Upper surface color: commonly near Green Group 137A. Under surface color: commonly near Green Group 138B more or less suffused with near Greyed-Red Group 178B.

*Adult foliage*.—Upper surface color: commonly near Green Group 137A. Under surface color: commonly near Yellow-Green Group 147B.

Leaflets:

*Shape*.—Tip: acuminated. Base: obtuse.

*Texture*.—Leathery.

*General appearance*.—Oval.

*Edge*.—Slightly denticulate.

*Serration*.—Small and single.

*Petiole rachis*.—Color of upper surface: commonly near Yellow-Green Group 146C. Color of under surface: commonly near Yellow-Green Group 146B.

*Petioles*.—Upper surface: no glandular. Under surface: few prickles. Color of upper surface: commonly near Yellow-Green Group 146C. Color of under surface: commonly near Yellow-Green Group 147C. Petiole length of terminal leaflet: approximately 3.2 cm on average.

*Stipules*.—General appearance: adnate, pectinate and rather broad. Length: approximately 2.1 cm on average. Width: approximately 0.7 cm on average. Color of upper surface: commonly near Yellow-Green Group 146C. Color of under surface: commonly near Yellow-Green Group 146B.

Inflorescence:

*Number of flowers per stem*.—Generally between 1 to 5 flowers per stem.

*Lastingness of bloom*.—Typically near one week on average.

*Bud*.—Shape: conical. Size: medium. Length: approximately 1.5 cm on average. Width: approximately 1.1 cm on average. Color as calyx breaks: upper surface: commonly between near Yellow Group 7A and Yellow Group 7C more or less bordered with Red Group 44A. under surface: commonly between near Yellow Group 7A and Yellow Group 7C more or less bordered with Red Group 44A.

*Sepals*.—Length: approximately 3.2 cm on average. Width: approximately near 0.8 cm on average.

Shape: with some extensions, length commonly near 1.0 to 3.0 cm on average, and width approximately 0.5 cm on average; at the top: elongated and narrow, at the base: upright. Upper surface: texture: tomentous. color: commonly near Yellow-Green Group 148C. Under surface: texture: smooth. color: commonly near Yellow-Green Group 144A.

*Receptacle*.—Color: commonly near Yellow-Green Group 144A. Length: approximately 0.6 cm on average. Width: approximately 0.6 cm on average. Surface: smooth. Shape: funnel shaped.

*Peduncle*.—Length: approximately 3.8 cm on average. Width: approximately 0.2 cm on average. Surface: smooth. Color: commonly near Yellow-Green Group 144B.

*Flower*.—Average diameter when open: commonly between near 8.0 to 9.0 cm on average. Borne: commonly between 1 to 5 flowers per stem. Shape: cup shaped. Number of petals under normal conditions: approximately 14 to 16 petals on average. Shape of the petal: base: obtuse. top: rounded. Texture of the petal: leathery. Petal length: approximately 4.6 cm on average. Petal width: approximately 3.2 cm on average. Petal arrangement: imbricated Petal drop: petals drop off cleanly before drying. Fragrance: none. Color when opening: upper surface: commonly near Yellow Group 8B amply suffused with near Red Group 44A and Red Group 50A. under surface: commonly near Yellow Group 8C bordered with near Red Group 44B. Color of the open flower: Upper surface: commonly near Yellow Group 8D amply suffused with near Red Group 44A and Red Group 45A. under surface: commonly near Yellow Group 8D more or less bordered and sometimes suffused with near Red Group 44B. Petaloids: number: typically one or two per flower. length: typically between 1.5 to 2.3 cm on average. width: typically between 0.4 to 0.9 cm on average. color in the course of opening: commonly near Yellow Group 13A amply suffused with near Orange-Red Group 30A. color when open: commonly near Orange-White Group 159D amply suffused with near Red Group 52B. Anthers: number is approximately 72 on average, length is approximately 0.2 cm on average, coloration is commonly between near Yellow-Green Group 144B and Yellow-Green Group 144C, and arrangement is regular around styles. Filaments: length is approximately 0.4 cm on average and coloration is commonly near Yellow Group 8C. Styles: length is approximately 0.1 cm on average, coloration is commonly near Yellow Group 3D, and number is approximately 87 on average. Stigmas: size is approximately 0.3 cm on average and coloration is commonly near Orange-Red Group 34A. Pollen: not available at this stage. Hips: not available at this stage.

Development:

*Vegetation*.—Very strong.

*Blooming*.—Early in the season, very abundant and nearly continuous.

*Winter hardiness/cold tolerance/drought/heat tolerance*.—Hardy zone is 5.

*Tolerance to disease*.—Good, and particularly against black spot (*Diplocarpon rosae*).

The new 'MEISISTOMA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Grandiflora Rose plant characterized by the following combination of characteristics:

(a) forms attractive, cup shaped, yellow amply suffused with red colored flowers, wherein the red coloration intensifies gradually in the course of opening, (b) provides, very dense, semi-glossy foliage, (c) exhibits good tolerance to diseases, particularly against black spot, and (d) is well suited for providing attractive ornamentation; substantially as herein shown and described.

* * * * *

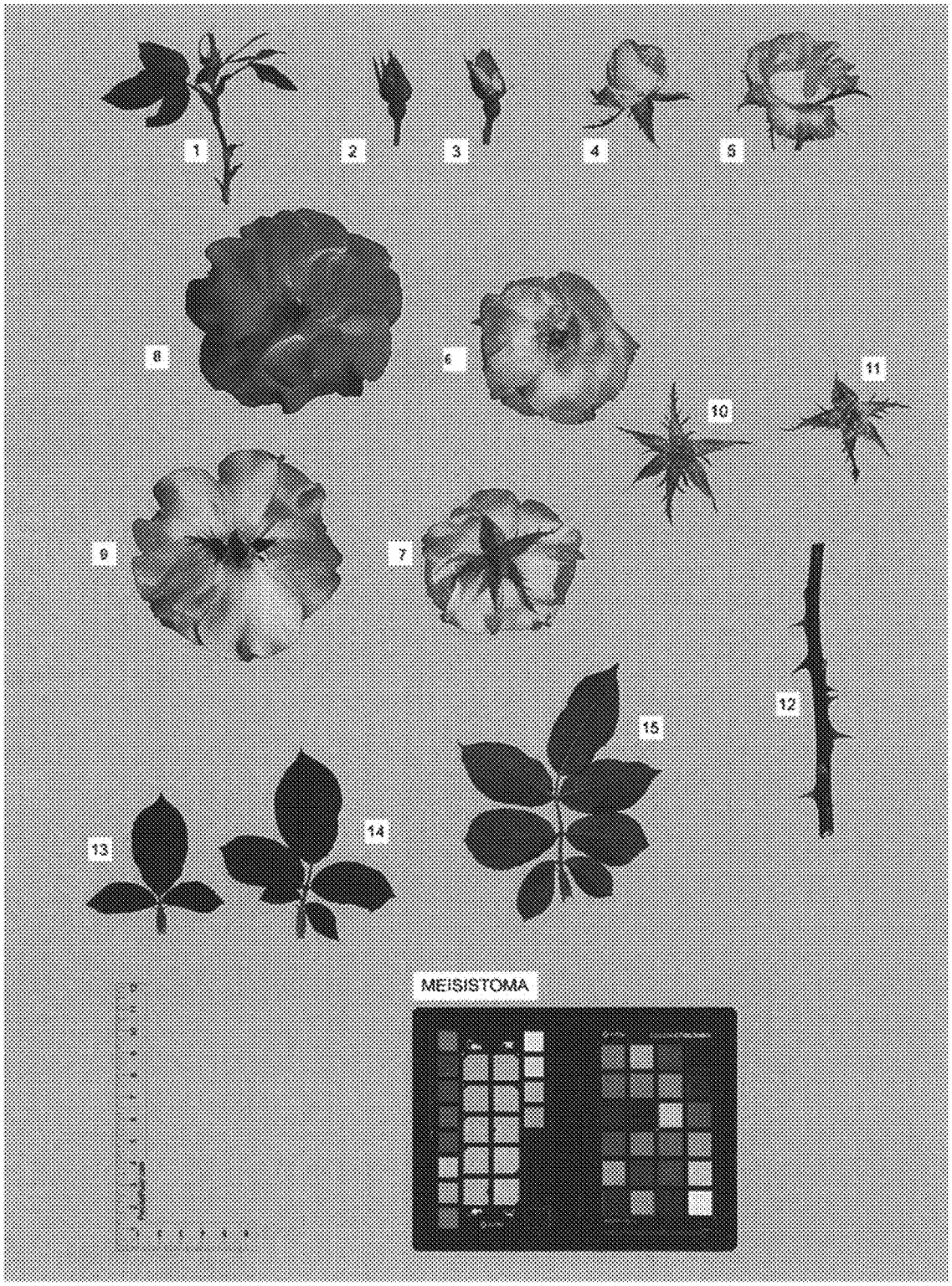
1
2
3
4
5
8
6
11
10
9
7
12
15
13
14
MEISISTOMA